United States Patent [19]

Livingston

[11] 4,404,853
[45] Sep. 20, 1983

[54] METHOD AND APPARATUS FOR ULTRASONIC TESTING OF TUBULAR GOODS

[76] Inventor: Waylon A. Livingston, 2534 Hollywood, Norman, Okla. 73069

[21] Appl. No.: 242,833

[22] Filed: Mar. 12, 1981

[51] Int. Cl.³ .............................................. G01N 29/04
[52] U.S. Cl. ......................................... 73/622; 73/628
[58] Field of Search ................. 73/628, 622, 637, 638, 73/640, 641

[56] References Cited

U.S. PATENT DOCUMENTS

| 4,041,773 | 8/1977 | Hauldren et al. ..................... 73/638 |
| 4,217,782 | 8/1980 | Pont ...................................... 73/637 |

FOREIGN PATENT DOCUMENTS

| 2806550 | 8/1979 | Fed. Rep. of Germany ........ 73/622 |
| 2027199 | 2/1980 | Fed. Rep. of Germany ........ 73/622 |
| 1400484 | 4/1965 | France .................................. 73/622 |
| 52-53486 | 4/1977 | Japan .................................... 73/637 |

Primary Examiner—Anthony V. Ciarlante
Attorney, Agent, or Firm—Laney, Dougherty, Hessin & Beavers, Inc.

[57] ABSTRACT

Method and apparatus for ultrasonic testing of tubular goods wherein plural circumferential arrays are utilized for continuous testing for specifically oriented defects. The apparatus utilizes plural ultrasonic energy transducers disposed in circumferential array for transmitting and receiving ultrasonic energy toward a central bore area. Further support structure serves to dispose the tubular goods in the central bore area for movement relative to said plural ultrasonic energy transducers while fluid enclosure means, also including a central bore area as defined by a slidable seal, maintains a fluid environment between each of the plural ultrasonic energy transducers and the tubular goods. The plural ultrasonic transducers are then repetitively energized and received energy variations due to discontinuities in said elongate goods are then output as an indication of quality.

30 Claims, 17 Drawing Figures

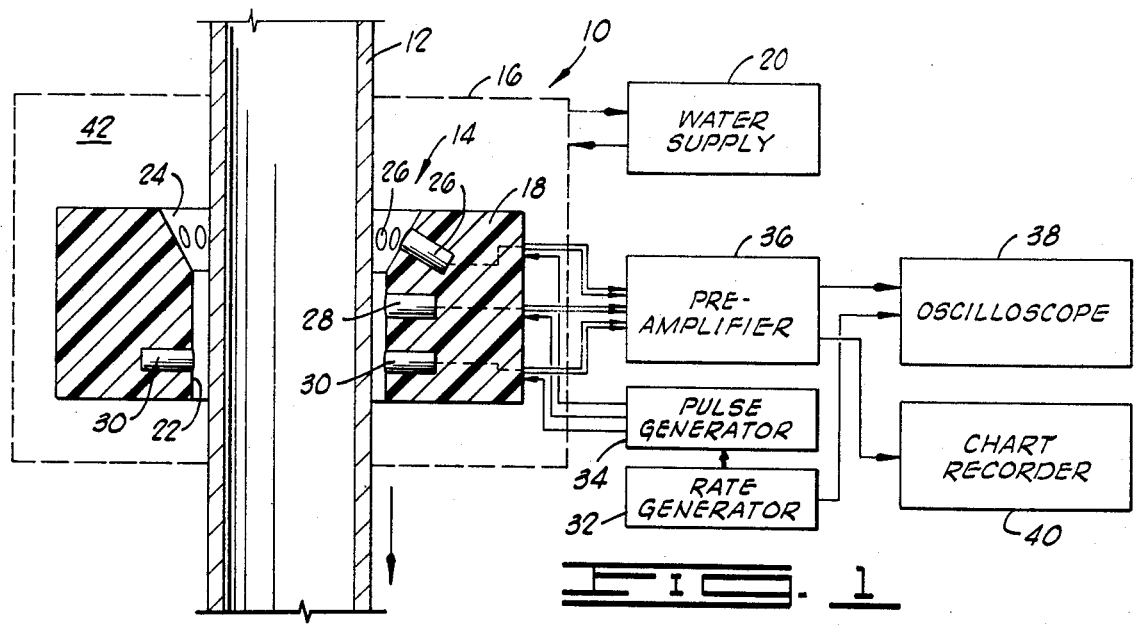
FIG. 1
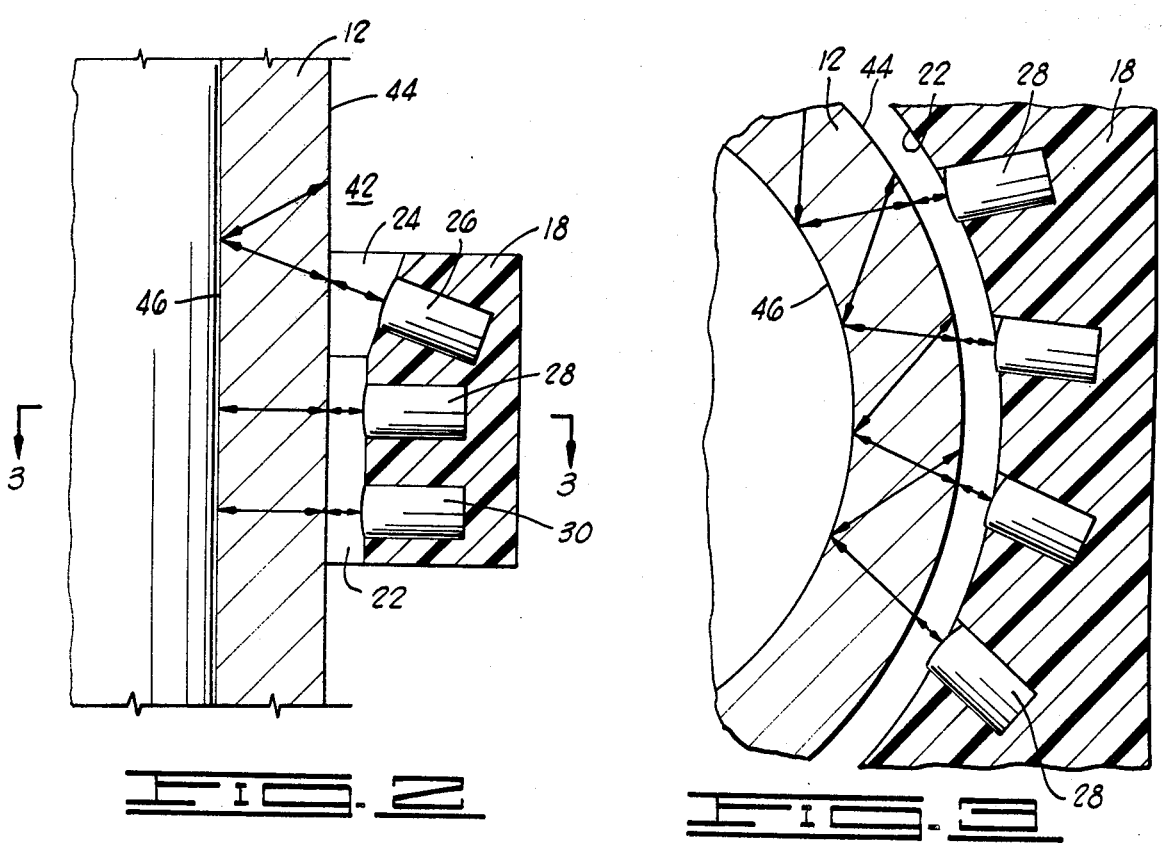
FIG. 2
FIG. 3

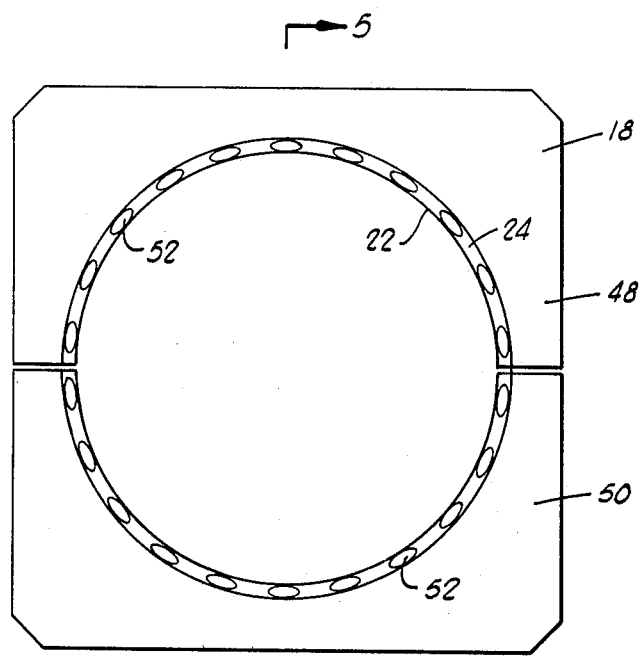
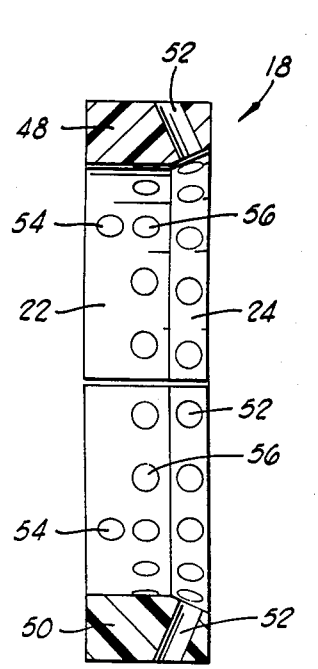
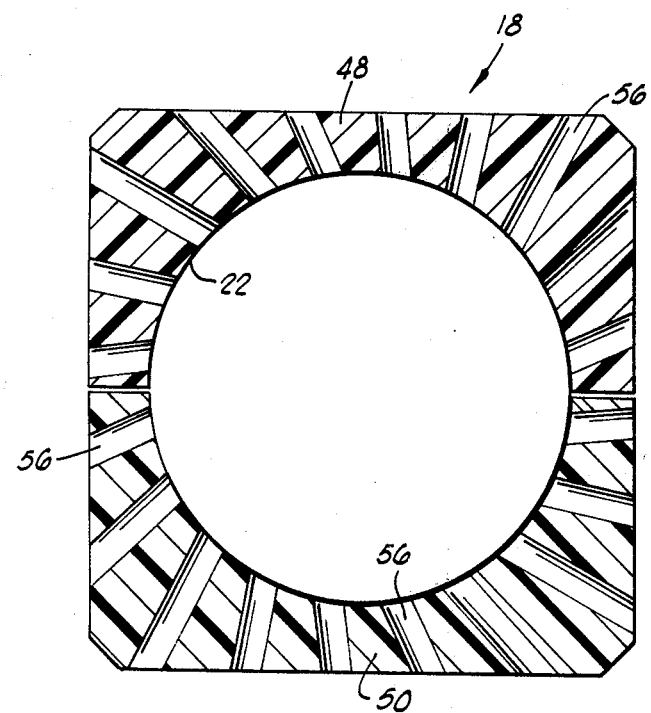
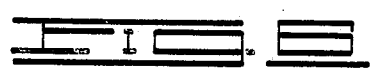

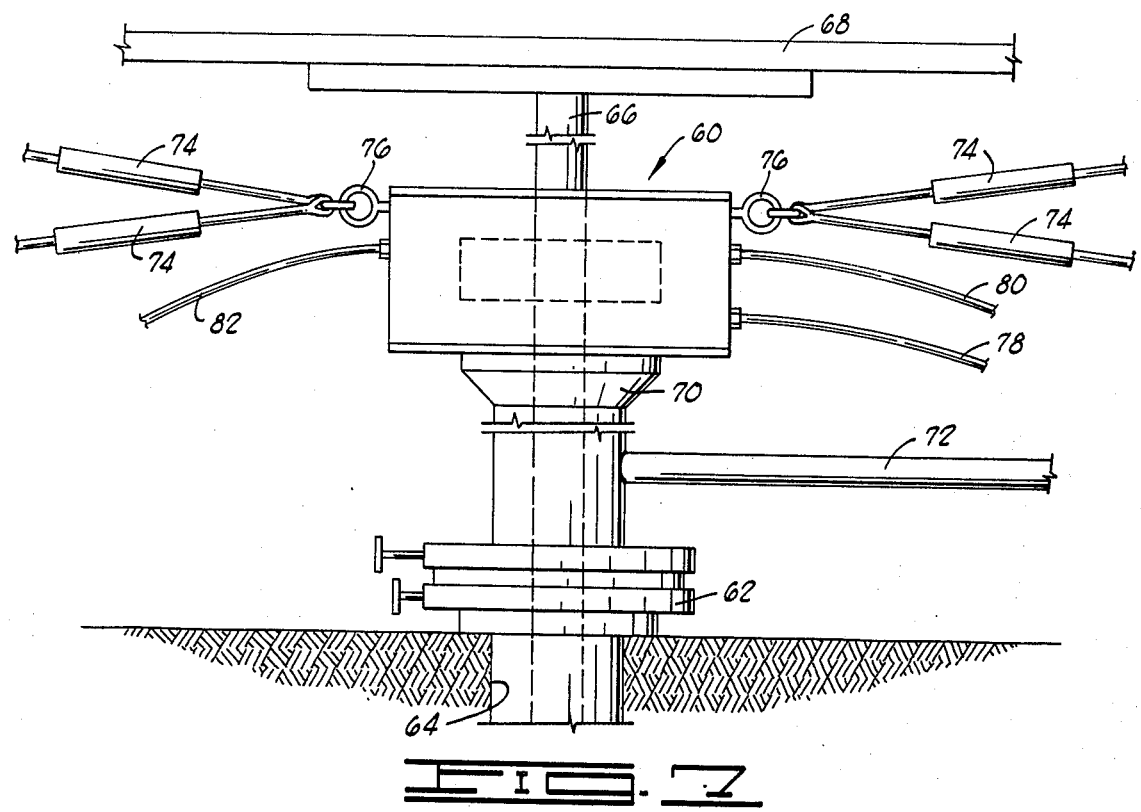
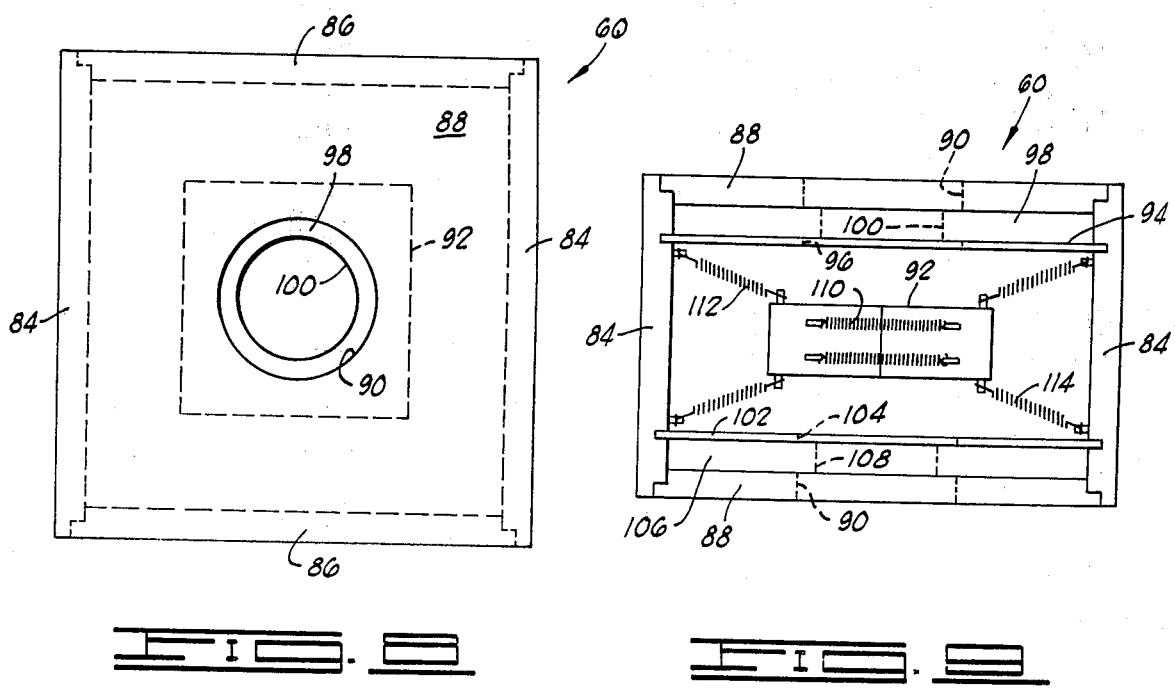

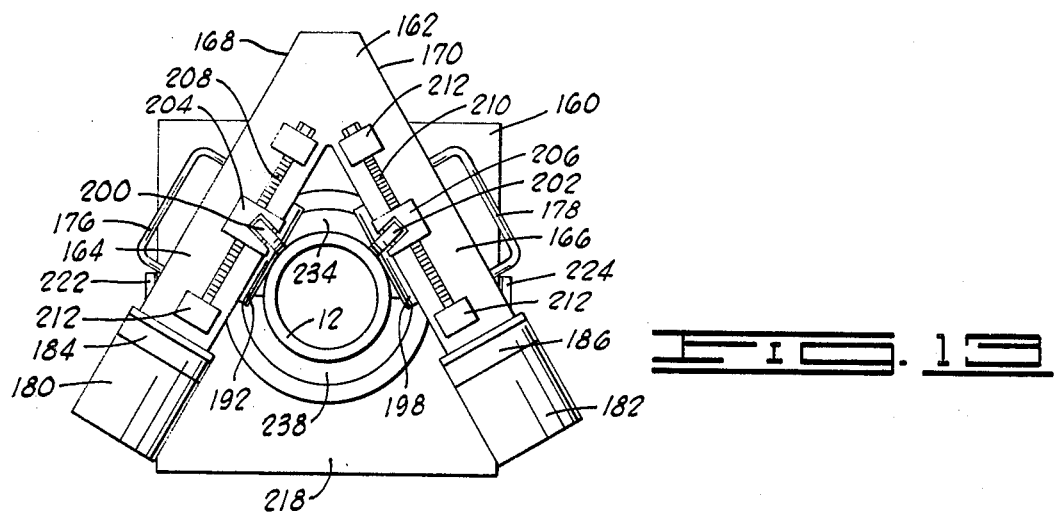
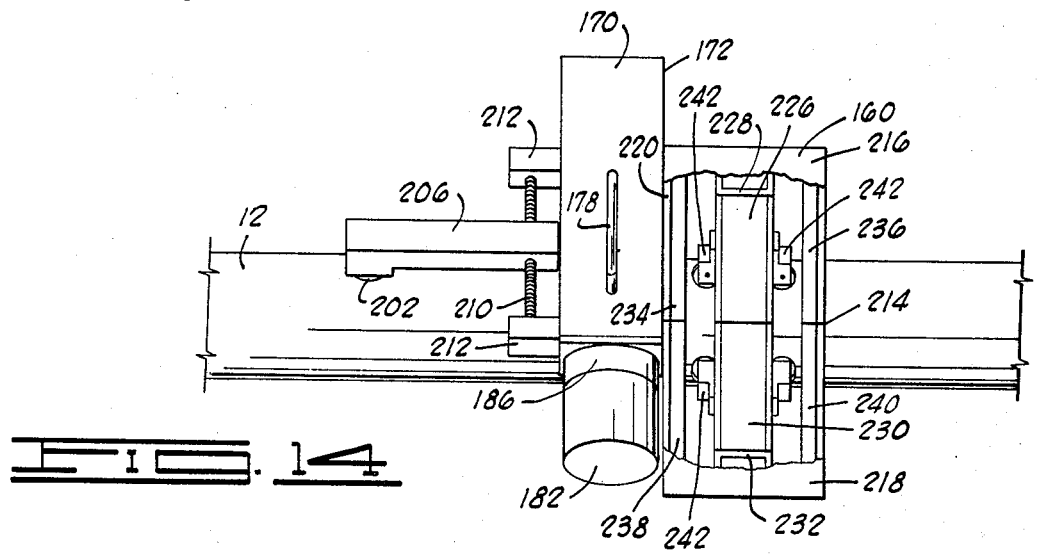
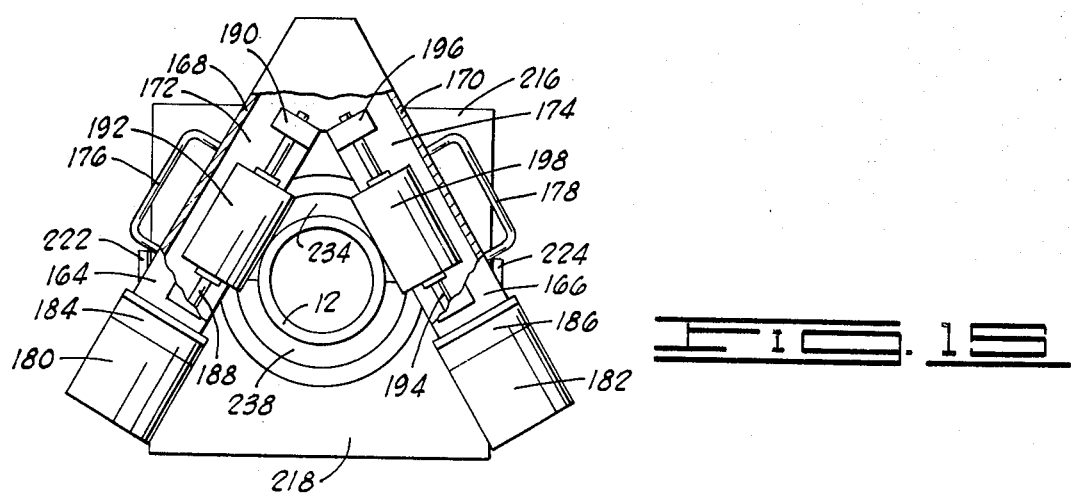

METHOD AND APPARATUS FOR ULTRASONIC TESTING OF TUBULAR GOODS

BACKGROUND OF THE INVENTION

1. Field of the Invention

The invention relates generally to method and apparatus for ultrasonic testing of generally uniform cross-section elongate goods and, more particularly, but not by way of limitation, it relates to improved apparatus for defect detection in tubular goods such as oil well casing, drill pipe, tubing and the like.

2. Description of the Prior Art

The prior art includes numerous methods and varying forms of apparatus for ultrasonic testing of metallic objects or specimens, and such prior devices have functioned under a variety of techniques and energy coupling schemes to provide defect and/or discontinuity indication of the test specimens. It is only recently that attempts have been made to carry out large-scale ultrasonic testing of oil field tubular goods and particularly those methods which carry out the test operation with controlled relative movement between the testing cell and the specimen goods.

A prior U.S. Pat. No. 4,106,347 discloses use of a frame including a quadrature array of extendable cylinders for moving wheeled crystal transducer assemblies into contact with a drill pipe section at a position above the derrick floor during tripping operations. In this disclosure, four transducers functioning within water filled rubber wheels are maintained in contact with selected portions of the drill pipe in order to read any defects. Such systems must contend with extraneous readout of confusing nature due to interposition of diverse materials, such as the energy coupler and the rubber wheel container structure, prior to transmission of the ultrasonic energy into the specimen tubular goods. Direct normal positioning of the energy transducers further imposes limitations as to types and positions of defects that are detectable.

U.S. Pat. No. 3,533,281 discloses another form of ultrasonic testing wherein the plural ultrasonic energy transducers are rotated relative to the tubular goods undergoing test as it is moved longitudinally relative to the test section. Here again, ultrasonic energy transducers are aligned directly normal to the tubular goods and thus enable only a single testing mode of the specimen material. U.S. Pat. No. 3,540,267 discloses yet another form of drill pipe testing device wherein the drill pipe is rotated and/or flexed during testing to provide tension and compression stressing during inspection by relatively conventional ultrasonic energy transducer assemblies.

SUMMARY OF THE INVENTION

The present invention relates to an improved method and apparatus for ultrasonic testing of tubular goods, particularly tubular goods as tested while in longitudinal motion relative to the test apparatus. More particularly, the invention consists of a circular array of ultrasonic transducers which examine for each of transverse and longitudinal defects while additional transducers within the same array verify wall thickness of the tubular specimen. Slidable seal enclosure means maintains fluid energy couplant in envelopment of the circular array while allowing axial movement of the test specimen relative thereto. The ultrasonic testing array assembled in coaction with the energy couplant enclosure is then utilized with associated support apparatus for testing within the oil well derrick structure during tripping operations; or for yard testing in place of horizontally stored tubular goods; or for testing of tubular goods as longitudinally moved therethrough. Thus, in addition to the testing array and enclosure apparatus being operatively supported within the derrick structure, the array and enclosure may be constructed with attached motive means for carrying the array along the horizontal tubular goods while testing, or the array and enclosure may be associated with stationary support structure including motive means for driving the tubular goods axially through the array while testing.

Therefore, it is an object of the present invention to provide an ultrasonic test apparaus for tubular goods that effects plural modes of examination simultaneously.

It is also an object of the invention to provide a tubular goods testing device which can be operated in any of plural attitudes to enable testing of oil field tubular goods, either new or used, in operational or storage position, and without need for rotation of the tubular goods.

It is yet further an object of the present invention to provide a device for inspection of oil field tubular goods that may be bent or twisted.

It is still further an object of the invention to provide a pipe testing device that is fire hazard allowable and suitable for use on board offshore oil rigs.

Finally, it is an object of the present invention to provide an ultrasonic inspection device situated beneath the derrick floor for continuous inspection of oil field tubular goods during tripping operations.

Other objects and advantages of the invention will be evident from the following detailed description when read in conjunction with the accompanying drawings which illustrate the invention.

BRIEF DESCRIPTION OF THE DRAWINGS

FIG. 1 is a block diagram of the elongate goods test device of the present invention;

FIG. 2 is a partial section of tubular goods and a transducer array illustrating ultrasonic energy paths as utilized in the present invention;

FIG. 3 is a partial section taken along lines 3—3 of FIG. 2;

FIG. 4 is a top plan view of a transducer array;

FIG. 5 is a vertical section taken along lines 5—5 of FIG. 4;

FIG. 6 is a cross-section of a transducer array block as taken through the center circumfery of transducer positions;

FIG. 7 is a view in elevation of an ultrasonic testing device in operational attitude within oil derrick structure;

FIG. 8 is a top view of the testing device of FIG. 7;

FIG. 9 is a side view of the testing device of FIG. 7 with side plate removed;

FIG. 13 is an alternative form of the present invention as it is utilized in combination with a motive assembly;

FIG. 14 is a side elevation of the testing device of FIG. 13;

FIG. 15 is a front view in elevation with parts shown in cutaway of the testing device of FIG. 13;

DETAILED DESCRIPTION OF THE INVENTION

Figure 10:
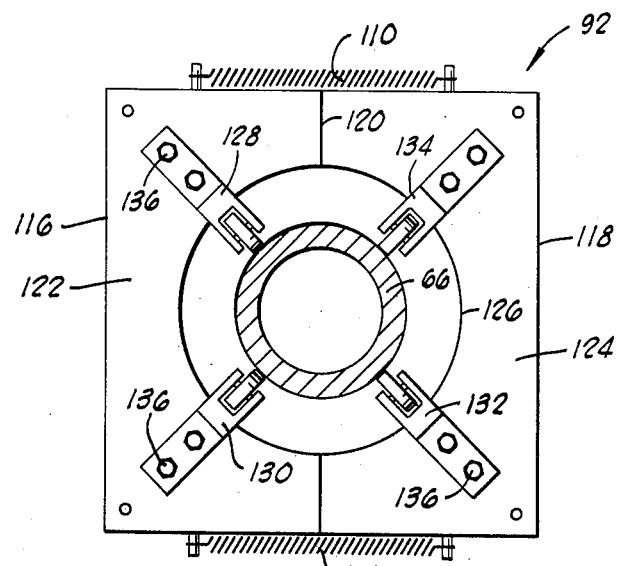
FIG. 10 is a top plan view of the array frame of the present invention.

Referring to FIG. 1, an ultrasonic testing device 10 functions to inspect tubular goods 12 utilizing a circular transducer array 14 within an energy coupling fluid enclosure 16. Transducer array 14 consists of an array block 18 as formed from such as aluminum, plexiglas or the like, and retaining a plurality of ultrasonic energy receiver-transmitter transducers in selected positioning around tubular goods 12. A fluid supply 20, e.g. water or suitable energy couplant, maintains the fluid enclosure 16 to a selected fill level and sealing members, to be described below, are maintained in contact with the tubular goods 12 at the top and bottom of enclosure 16.

The array block 18 is formed with a central bore 22 having bevel surface 24 formed at an angle of about 19° from vertical of the axis of bore 22. A first circumfery of transverse defect transducers 26 are then disposed in bevel surface 24 in equi-spaced disposition. Use of twenty-two such transverse transducers 26 provides very good circumferal coverage of tubular goods 12. Within central bore 22, a plurality of equi-spaced longitudinal defect transducers 28 are disposed. A lesser number of fourteen to eighteen longitudinal transducers 28 may be utilized. Finally, around the lower end of central bore 22 are disposed a plurality of wall thickness transducers 30. The wall thickness transducers 30 may be anywhere from two to eight in number and preferably equi-spaced in their circumfery about tubular goods 12. It is also contemplated that the wall thickness transducers 30 be interposed between rows of transducers 26 and 28 to provide additional energy isolation.

In each case, transducers 26, 28 and 30 may be selected from the commercially available ceramic types such as barium titanate, lead methaniobate, lead zirconate titanate, etc. The transducers are highly focused through convex grinding of the face and, in present design, the transverse and longitudinal defect transducers 26 and 28 are pulsed at 2.25 Megahertz while the wall thickness transducers 30 are pulsed at 5 Megahertz. A basic oscillator system or rate generator 32 provides system timing as it controls the rate of pulse generator 34 which, in turn, provides energizing input to the respective transducers 26, 28 and 30. Received energy from transducers 26, 28 and 30 is then applied to a multichannel preamplifier 36 for input to a plural data display oscilloscope 38 as also controlled from rate generator 32. A chart recorder 40 may also be utilized to indicate test data depending upon the operating mode and the exigencies of the application.

Received energy output from transverse transducers 26 may be applied in parallel to preamplifier 36; however, present design utilizes dual inputs as parallel from eleven transducers 26 each for indication to preamplifier 36. Similarly, the longitudinal transducers 28 are applied to parallel inputs from each of nine transducers 28, and wall thickness transducers 30 may be applied in parallel or gated inseparately for wall thickness indication. The associated electronics is largely conventional and commercially available although special purpose equipment and digitalized processing may be utilized. One form of commercially available equipment for carrying out the method may utilize a Model Mark IV Ultrasonic Flaw Detector as available from Sonic Instruments, Inc., in association with a Gould Model 2200 Chart Recorder.

FIGS. 2 and 3 illustrate in greater detail the disposition and directivity of the transmitter-receiver transducers 26, 28 and 30 as disposed in array block 18. A body of energy-coupling fluid 42, water, selected olins, etc., is of course maintained between the transducers 26-30 and the outer wall 44 of tubular goods 12. Each of the transverse defect transducers 26 is aligned within bevel surface 24 to direct transmitted ultrasonic energy radially at outer wall 44 and an axial angle of 19° to normal. This energy then undergoes refraction in accordance with the classical function (Snell's Law) and is directed to reflection from the inner wall of 46 of tubular goods 12 with a portion of the energy continuing on for reflection from outer wall 44. Reflected energy along this traverse then returns along essentially the same paths for detection by transducer 26. Any defect or discontinuity within the wall of tubular goods 12 will appear as an abnormal energy indication when viewed on the operating equipment. The wall thickness transducers 30 are pulsed at a higher frequency, e.g., 5 Megahertz, and are direct viewing normal to the outer wall 44 of tubular goods 12 to provide a straight-through path with detection of return energy. The return or received energy is then processed through a tolerance gate indication to indicate any variation in wall thickness as between inner wall 46 and outer wall 44.

Referring also to FIG. 3, the longitudinal transducers 28 are aligned normal to the axial dimension of tubular goods 12 but angled in the transverse plane to obtain a scan view of a section of the tubular goods wall. The longitudinal defect transducers 28 are mounted at an angle of 15.5° shifted transversely from the radial to provide shear waves within the pipe wall, this angle and spacing providing scan of sufficient arc sector of tubular goods 12 while also avoiding any interference as between transducrs 28, i.e., each transducer 28 can only receive its own reflected energy. Here again, ultrasonic energy directed from transducers 28 undergoes refraction at outer wall 44 with reflection from inner wall 46 and outer wall 44 for return back to transducer 28. Proper calibration of the operating sensitivity clearly differentiates the dual reflection path as indicated in the operating equipment.

FIG. 4 illustrates a complete array block 18 as it may be divided into two halves 48 and 50. A plurality of equi-spaced bores 52 are formed at proper angle in bevel surface 24, see also FIG. 5, the bores 52 receiving the transverse transducer 26. In like manner, and referring to FIG. 5, a plurality of equi-spaced bores 54, e.g., a quadrature array, are formed for reception of the wall thickness transducers 30. Referring also to FIG. 6, the mid-group or bores 56, in this case twenty, are similarly formed at their proper angular relationship in the plane transverse to central bore 22 of array block 18.

The array block 18 may be formed from such as aluminum, plexiglas, etc., and after formation of all bores 52, 54 and 56, the respective transmitter-receiver transducers may be bonded in position with the remainder of the bores sealingly filled with a suitable potting compound. Electrical leads, i.e., pulsing and receiver leads from each of the transducers, may then be interconnected in whatever the selected paralleling interconnection and potted within a groove (not shown) as formed about the periphery of block array 18 thereby to provide a single, watertight connector conduit for each respective bank or tier of transducers.

FIG. 7 illustrates a testing device 60 in installation within an oil well derrick. Thus, the installation includes the conventional equipment such as blowout preventers 62 covering borehole casing 64 with drill pipe 66 extending down through derrick rig floor 68. A casing and bell nipple 70 extend above blowout preventers 62 and the return mud line 72 is drawn therefrom. The ultrasonic testing device 60 is then semi-rigidly supported on bell nipple 70 by means of a plurality of spring lines 74 which attach to the derrick superstructure under carriage. Eye bolts 76 are provided on the frame of testing device 60 for securing while fluid level control is enabled via inlet conduit 78 and outlet conduit 80, and electrical connections are made via conduit 82. Thus, testing device 60 is secure above bell nipple 70 yet has sufficient freedom of movement of shift laterally with any shifting of drill pipe 66 within borehole casing 64.

FIGS. 8 and 9 illustrate testing device 60 as it consists of a fluid enclosure formed by side plates 84, front and back plates 86 and top and bottom plates 88. Top and bottom plates 88 each include a central bore 90 through which the workpiece passes vertically, and an array frame 92 is suspended in alignment with upper and lower bores 90. An upper panel 94 having a central bore 96 is secured between side plates 84, and a rigid rubber sealing member 98 having a narrowed bore 100 is retained between upper panel 94 and upper plate 88. In like manner, a lower panel 102 having central bore 104 is secured between side plates 84 to retain a lower rubber panel or sealing member 106 having bore 108 in secure juxtaposition against bottom plate 88.

The array frame 92 is constructed as spearable halves and is retained in the operative position by means of retaining springs 110, and array frame 92 may be suspended in operative position within the fluid enclosure of device 60 by means of a suitable quadrature array of upper retaining springs 112 and lower retaining springs 114. Conventional fastening and securing techniques may be utilized in construction of the testing device 60.

Figure 11:
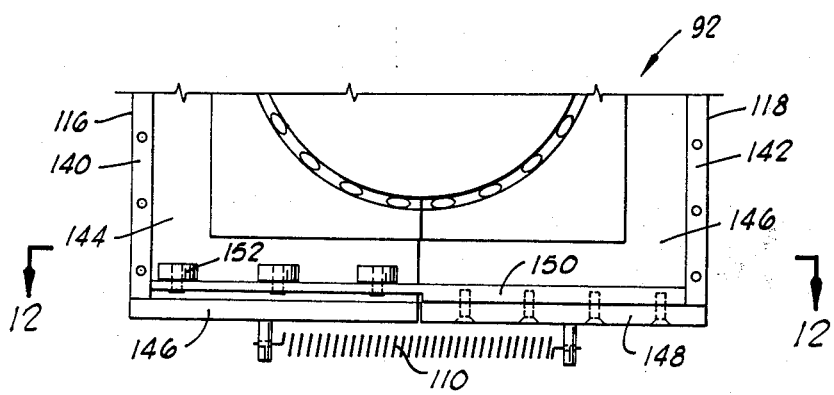
FIG. 11 is a partial top view of the array frame with top plate removed.
Figure 12:
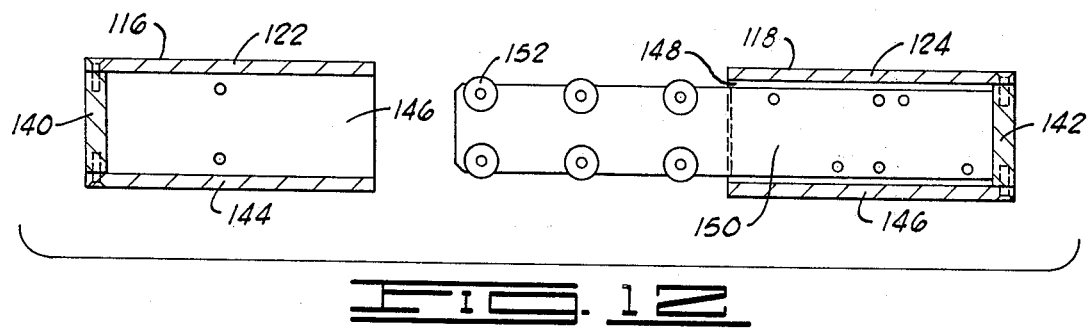
FIG. 12 is a section in exploded form as taken on lines 12—12 of FIG. 11.

FIGS. 10, 11 and 12 illustrate a basic array frame 92 in greater detail. Referring to FIG. 10, the array frame is separable into two halves 116 and 118 as separated along inner edges 120. Halves 116 and 118 include a top plate 122, 124 which cooperate to define a bore 126 through which the test piece or drill pipe 66 passes. The top plates 122 and 124 then may include a quadrature array of guide rollers 128, 130, 132 and 134 which are each adjustably mounted by fasteners 136 to enable radially inward positioning to accommodate various sizes of workpiece, i.e., drill pipe, casing, tubing and the like. It should be noted that guide rollers 128, 130, 132 and 134 are not required in vertical testing applications such as that of FIGS. 7, 8, and 9, but only in longitudinal applications as will be further described below.

As shown in FIG. 11, with top plates removed, the array frame 92 includes opposite side panels 140 and 142 are adjoined to mating bottom plates 144 and 146, respectively. The frame half 116 includes opposite end panels 146 while opposite frame half 118 includes opposed end panels 148. The array frame half 118 also includes a guide roller assembly (see FIG. 12) consisting of a plate 150 and a plurality of guide rollers 152 suitably mounted as with fasteners to the inner side of opposite end plates 148. Thus, the guide roller assemblies function to guide and properly align the opposite frame halves 116 and 118 as they are initially assembled around a workpiece into operative position.

FIGS. 13, 14 and 15 illustrate on alternative form of the invention wherein the basic fluid enclosure and ultrasonic testing array are utilized with motive means enabling progression along a tubular goods specimen when in the horizontal attitude. This buggy-type testing apparatus may be utilized with either new or used tubular goods as it may be placed in storage areas. Thus, referring to FIG. 13, a fluid enclosure box 160, including the basic type of transducer array, is coupled with a drive assembly 162 such that the unit may be manually placed on horizontally stored tubular goods and energized to traverse therealong while continuously testing the goods with ultrasonic energy scanning. The drive assembly 162 consists of a main chassis of inverted V-shape consisting of front plates 164, 166, side plates 168, 170, and rear plates 172, 174. Gripping handles 176 and 178 are weld-secured to the respective side plates 168 and 170 to enable manual handling and positioning of the tester.

Electric drive motors 180 and 182 are suitably mounted with respective gear boxes 184 and 186 on respective lower ends of the chassis channel members. As shown in FIG. 15, motor 180 and gear box 184 provided rotational input on a drive shaft 188 as journaled in a bearing mount 190 (FIG. 15) and carrying a drive wheel 192 in gripping contact with tubular goods 12. Similarly, drive motor 182 and gear box 186 provide rotational input to a drive shaft 194 as journaled in bearing mount 196 and carrying a drive wheel 198 in gripping contact with tubular goods 12 on the opposite side. The bearing mounts 190 and 196 may be such as weld-secured to respective rear plates 172 and 174; and, the drive wheels 194 and 198 may be formed of suitable soft rubber, splined steel rollers or the like, having good gripping characteristics for moving the tester along the tubular goods 12.

Referring also to FIG. 14, the forward end of the tester is maintained in balanced alignment by means of adjustable guide wheels 200 and 202 as carried on support arms 204 and 206. Each of support arms 204 and 206 is adjustably carried on respective adjusting screws 208 and 210 as mounted in spaced screw blocks 212 secured on front plates 164 and 166.

The fluid enclosure box 160 is constructed of generally cubical form but it is formed to be bisectable along the horizontal midline 214 to form upper and lower container sections 216 and 218. Upper container section 216 is positioned with the front panel 220 secured as by welding to the rear plate 172 of drive assembly 162. The lower section 218 is removable and sealably positionable in fluid-tight coaction with upper section 216 by means of latch hinges 222 and 224.

Upper section 216 includes a semi-circular section of transducer array frame 226 as affixed by a bracket 228 within upper section 216. In similar manner, the lower enclosure section 218 includes a mating semi-circular transducer array frame 230 as affixed on a mounting bracket 232 within lower section 218. The transducer arrays within frame sections 226 and 230 may be constructed in like manner to those previously disclosed with each of transverse defect, longitudinal defect and wall thickness transducers aligned for inspection of the tubular goods 12.

Rubber seal sections 234 and 236 are removably secured adjacent the respective forward wall 220 and rear wall of upper section 216 for positioning in sealing engagement around tubular goods 12. Also, lower section 218 includes forward and rear rubber seals 238 and 240.

Upper and lower disposed adjustable guide rollers 242 (rollers 128-134, FIG. 10) are disposed on each side of array frame 226 and 230, and these rollers may be adjustably positioned in accordance with the diameter of tubular goods 12 undergoing test. In like manner, the rubber seals 234, 236, 238 and 240 would be replaced with seals defining the proper diameter of aperture, and the forward guide arm 206 would be adjustably positioned by rotation of the screw 210 for proper coaction and alignment with tubular goods 12 to maintain the tester in a balanced attitude during operation.

In operation, the tester may be manually placed on a section of tubular goods 12 to be tested whereupon the lower enclosure section 218 is placed in sealing engagement and latched into position around tubular goods 12. Thereafter, energy couplant fluid is introduced to fill the internal void of enclosure 160 and the electric drive motors 180 and 182 are energized to move the tester along the tubular goods section 12. As the tester moves, the transducer array is under continuous pulsed energization with readout being applied to an operator station. The fluid enclosure 160 holds more than enough water such that leakage is minimal during traverse of the tester along a normal length of tubular goods 12 and fluid refill of enclosure 160 may be carried out each time the tester is repositioned for a traverse along a tubular goods section; however, continual supply and drainage can be applied to maintain the fluid enclosure 160 full during some special operations of the testing unit.

Figure 16:
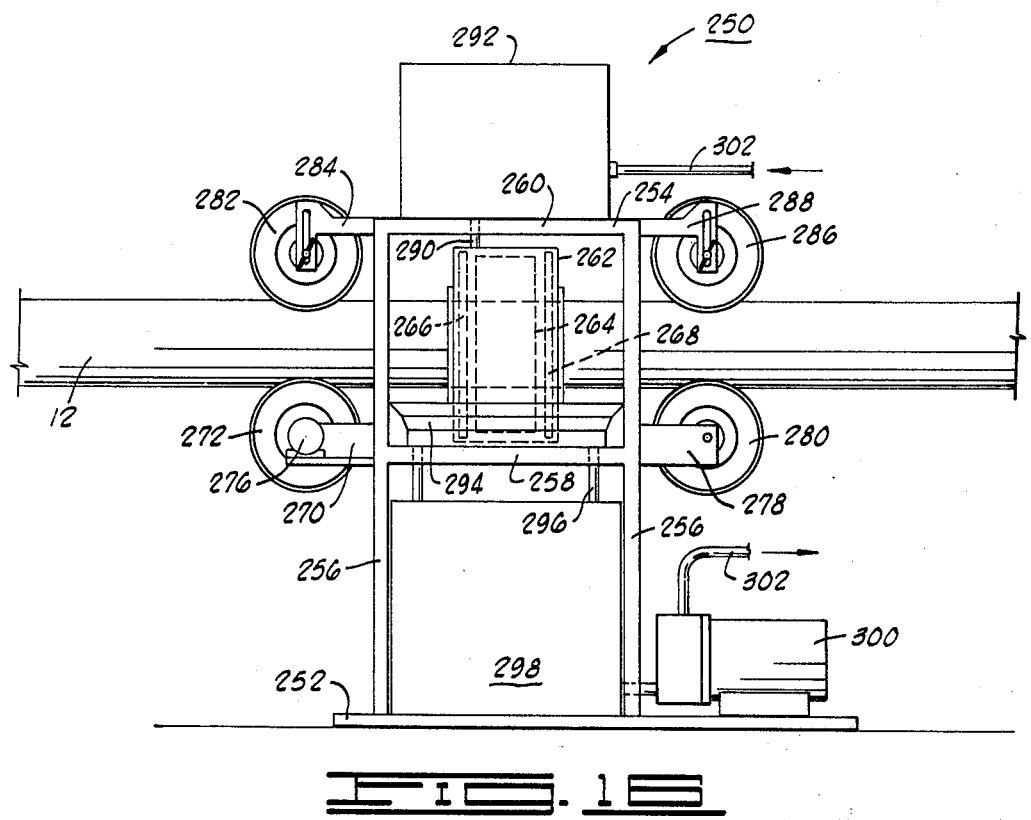
FIG. 16 is a second alternative embodiment of the present invention wherein the testing device is used in combination with stationary structure.
Figure 17:
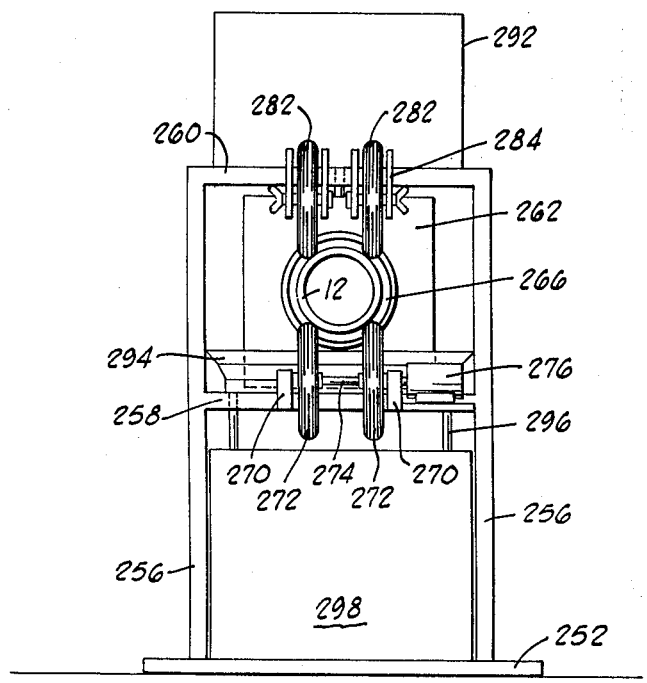
FIG. 17 is a front view in elvation of the testing device of FIG. 16.

Referring to FIGS. 16 and 17, a stationary testing unit 250 is suitably supported on a base 252 to receive tubular goods 12 for driven movement therethrough as ultrasonic testing is effected. The device 250 includes a frame 254 having a plurality of vertical upright members 256 in support of transverse frame members 258 and top frame members 260. A testing enclosure box 262 is removably supported between transverse frame members 258 and 260. Enclosure box 262 may be similar in all respects to those previously discussed which include a transducer array frame 264 having the requisite transducer array with transverse defect, longitudinal defect and wall thickness transducers. The front and back entries to enclosure box 262 are then suitably sealed by rigid rubber sealing means 266 and 268 which maintain a quiescent fluid environment within box 262. Array frame 264 may include the adjustable guide rollers 128-134 as shown in FIG. 10.

Support brackets 270, as secured to transverse member 258, support drive wheels 272 on a drive shaft 274 as rotated by a drive motor 276. On the opposite side of frame 254, support brackets 278 support a pair of idler wheels 280 in proper spacing to support the tubular goods 12 in balanced attitude during its passage through testing device 250. A pair of forward tension rollers 282 are supported on an adjustable support bracket 284, and rear tension rollers 286 are similarly supported in an adjustable support bracket 288 as secured from transverse top frame 260. The forward and rearward tensions rollers 282 and 286 may be adjustably set in elevation to accommodate various sizes of tubular goods 12.

Fluid for energy coupling is continually supplied to the transducer enclosure box 262 by means of inlet tube 290 from a storage tank 292. Leakage of fluid from the enclosure box 262 is then caught within a splash pan 294 supported within transverse frame 258, and the leakage fluid is then flowed through conduits 296 into reservoir 298. Fluid from the reservoir 298 is continually circulated by a motor driven pump 300 via conduit 302 for return to the upper storage tank 292. Preferably, storage tank 292 includes FILL and REFILL float switches in control of pump 300 to maintain proper level of fluid therein.

The stationary testing device 250 is suitable for use in ultrasonic testing of elongate tubular goods either new or used. The tubular goods 12 may be entered within enclosure box 262 whereupon fluid fill is effected; thereafter, the transducer testing array is energized in accordance with operator requirements and drive motor 276 moves the tubular goods 12 through the enclosure box 262 at a uniform rate as testing proceeds. Adjustment of the tension rollers 282 and 286 enable acceptance of a combination of diverse sizes of tubular goods, and the size and positioning of transducer enclosure box 262 may also be varied in accordance with the exigencies of the particular operations.

The foregoing discloses a novel approach to continuous ultrasonic testing of tubular goods and the several forms of specific apparatus to enable testing of tubular goods in operational attitude, in storage attitude, in assembly line handling, etc. The specific form of transducer array provides a greater degree of scanning coverage of the specimen while simultaneously examining for each of transverse defects or discontinuities, longitudinal discontinuities and wall thickness of the goods. Testing consistency is of high reliability since the system remains constant after initial set-up and calibration of the ultrasonic control circuitry.

Changes may be made in combination and arrangement of elements as heretofore set forth in the specification and shown in the drawings; it being understood that changes may be made in the embodiments disclosed without departing from the spirit and and scope of the invention as defined in the following claims.

What is claimed is:

1. Apparatus for ultrasonic testing of tubular goods, comprising:
   array block means defining a cylindrical central bore area;
   plural ultrasonic energy transducers secured in said block means for transmitting and receiving ultrasonic energy toward said central bore area, said plural transducers including a first equi-spaced circumferential array of transducers for detecting transverse discontinuities and a second equi-spaced circumferential array of transducers for detecting longitudinal discontinuities;
   means for disposing tubular goods in said central bore area for movement relative to said plural ultrasonic energy transducers;
   fluid enclosure means including a central bore area defined by a slidable seal for maintaining a fluid environment between each of said plural ultrasonic energy transducers and said tubular goods; and
   means for energizing said plural ultrasonic transducers and indicating received energy variations due to discontinuities in said tubular goods.

2. Apparatus as set forth in claim 1 wherein:
   said first circumferential array of transducers are each disposed at a selected acute angle relative to normal to the longitudinal axis of said tubular goods; and said second circumferential array of transducers are each disposed at a selected acute angle relative to the radial dimension of said tubular goods as aligned in a plane normal to said tubular goods.

3. Apparatus as set forth in claim 2 which further includes:
a third circumferential array of transducers each disposed normal to the longitudinal axis of said tubular goods.

4. Apparatus as set forth in claim 1 wherein:
said block means is an aluminum formation defining said central bore area therethrough.

5. Apparatus as set forth in claim 4 wherein:
said block means is suspended resiliently in position within said fluid enclosure means.

6. Apparatus as set forth in claim 1 wherein said fluid enclosure means comprises:
an enclosure having watertight sides and first and second end panels, said first and second end panels each having a central bore area; and
first and second resilient seal members each disposed inwardly adjacent the respective first and second end panels, and each defining said central bore area.

7. Apparatus as set forth in claim 6 which further includes:
a source of fluid connected for input to said enclosure; and
an overflow fluid outlet connected to said enclosure.

8. Apparatus as set forth in claim 6 wherein:
said first and second resilient seal members are replaceable to adjust the size of the central bore slidable seal.

9. Apparatus as set forth in claim 6 which further includes:
a frame means supporting said block means with each of said plural ultrasonic energy transducers in operative position between said first and second resilient seal members.

10. Apparatus as set forth in claim 1 wherein said means for disposing comprises:
a well drilling platform and associated elongate goods control mechanism for moving said elongate goods through said central bore area at a controllable rate.

11. Apparatus as set forth in claim 10 which is further characterized in that:
said plural ultrasonic transducers and fluid enclosure means are resiliently secured beneath the well drilling platform.

12. Apparatus as set forth in claim 11 wherein:
said tubular goods is drill pipe sections in coupled thread-end box-end engagement.

13. Apparatus as set forth in claim 10 wherein said fluid enclosure means comprises:
an enclosure having watertight sides and first and second end panels, said first and second end panels each having a central bore area; and
first and second resilient seal members each disposed inwardly adjacent the respective first and second end panels, and each defining said central bore area.

14. Apparatus as set forth in claim 13 which further includes:
a source of fluid connected for input to said enclosure; and
an overflow fluid outlet connected to said enclosure.

15. Apparatus as set forth in claim 14 wherein said means for disposing comprises:
means for supporting said elongate goods in a generally horizontal attitude; and
drive means for moving said plural transducers and water enclosure means along said elongate goods at a controllable rate.

16. Apparatus as set forth in claim 15 wherein said drive means comprises:
drive frame means secured to said water enclosure means;
motor means secured on said drive frame means; and
drive wheel means rotatably driven by said motor means in gripping contact with said tubular goods.

17. Apparatus as set forth in claim 16 wherein:
said drive frame means is an inverted V-shape with motor means mounted at each lower extremity to drive oppositely disposed dual drive wheel means in gripping contact with said tubular goods.

18. Apparatus as set forth in claim 16 which further includes:
a third circumferential array of transducers for detecting wall thickness of said tubular goods.

19. Apparatus as set forth in claim 15 which is further characterized in that:
said plural transducers and water enclosure means are sealably bisectable to enable manual placement of said ultrasonic testing apparatus on the tubular goods.

20. Apparatus as set forth in claim 1 wherein said means for disposing comprises:
means for supporting said elongate goods while moving said elongate goods through said plural transducers and water enclosure means.

21. Apparatus as set forth in claim 20 wherein said means for supporting comprises:
upright frame means including base support and upper frame supporting said plural transducers and water enclosure means; and
drive means including drive wheels in gripping engagement with said tubular goods for moving the tubular goods horizontally through said central bore area.

22. Apparatus as set forth in claim 21 wherein:
said first and second resilient seal members are replaceable to adjust the size of the central bore slidable seal.

23. Apparatus as set forth in claim 21 which further includes:
water supply means providing input to said water enclosure means; and
means collecting water escaping from said enclosure means for redirection back to said water supply means.

24. Apparatus as set forth in claim 23 which further includes:
a third circumferential array of transducers for detecting wall thickness of said tubular goods.

25. Apparatus as set forth in claim 1 wherein:
said first circumferential array of transducers are each disposed at a selected acute angle relative to normal to the longitudinal axis of said tubular goods; and
said second circumferential array of transducers are each disposed at a selected acute angle relative to the radial dimension of said tubular goods as aligned in a plane normal to said tubular goods.

26. Apparatus as set forth in claim 25 which further includes:

a third circumferential array of transducers each disposed normal to the longitudinal axis of said tubular goods.

27. A method for ultrasonic testing of tubular goods, comprising:

moving said tubular goods longitudinally relative to a point of inspection;

repetitively pulsing and receiving return energy at said point of inspection from first and second circumferential arrays of ultrasonic energy transducers disposed in an array block, wherein the first circumferential array is directed with each transducer disposed at a selected acute angle relative to normal to the longitudinal axis of the tubular goods to detect transverse discontinuities, and the second circumferential array is directed with each transducer disposed at a selected acute angle relative to the radial dimension of said tubular goods as aligned in a plane normal to said goods to detect longitudinal discontinuities;

continually maintaining an energy-couplant fluid environment at said point of inspection; and indicating both transverse and longitudinal discontinuities detected along said tubular goods.

28. A method as set forth in claim 27 wherein:

said tubular goods is box-end thread-end coupled oil well drill pipe in operative disposition; and said point of inspection is located beneath the oil well drilling platform.

29. A method as set forth in claim 27 which further includes:

repetitively pulsing and receiving return energy at said point of inspection from a third circumferential array of transducers directed normal to the longitudinal axis of said tubular goods to detect wall thickness thereof.

30. A method as set forth in claim 29 wherein:

said first, second and third transducer arrays are energized at differing ultrasonic frequency thereby to eliminate interference as between arrays.

* * * * *